United States Patent [19]
Laghi

[11] Patent Number: 5,897,517
[45] Date of Patent: Apr. 27, 1999

[54] FABRIC REINFORCED ELASTOMER MATERIALS

[75] Inventor: Aldo A. Laghi, Clearwater, Fla.

[73] Assignee: Alps South Corporation, St. Petersburg, Fla.

[21] Appl. No.: 08/895,048

[22] Filed: Jul. 16, 1997

Related U.S. Application Data

[63] Continuation-in-part of application No. 08/739,242, Oct. 29, 1996, abandoned.

[51] Int. Cl.$^6$ ....................................................... A61F 13/00
[52] U.S. Cl. .................................................................. 602/62
[58] Field of Search ................................ 602/20–22, 26, 602/60, 62, 63, 75; 623/32–37

[56] References Cited

U.S. PATENT DOCUMENTS 5,497,513  3/1996  Arabeyre et al. ............................ 2/240

Primary Examiner—Richard J. Apley
Assistant Examiner—Kim M. Lee
Attorney, Agent, or Firm—Joseph C. Mason, Jr.; Dennis G. LaPointe

[57] ABSTRACT

A fabric reinforced elastomer material which is useful in the medical art is disclosed. The fabric reinforced elastomer material includes a first base material and a second base material. The present invention is useful for fashioning suspension sleeves, brace supports, cushion pads for orthosis devices and compression garments.

8 Claims, 4 Drawing Sheets

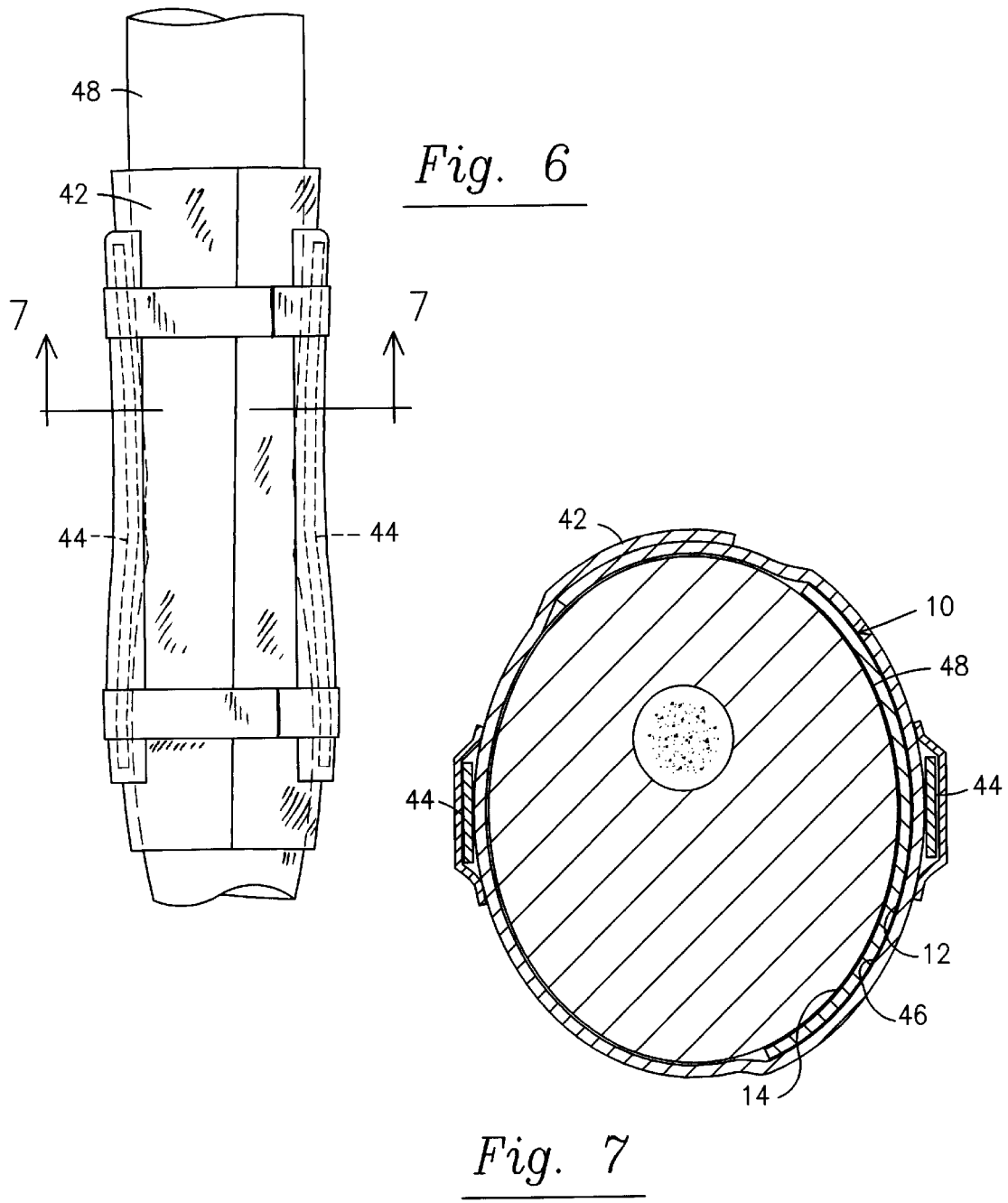

FABRIC REINFORCED ELASTOMER MATERIALS

This application is a continuation-in-part of application No. 08/739,242 filed on Oct. 29, 1996, now a abandoned.

FIELD OF THE INVENTION

This invention relates, generally, to a fabric reinforced elastomer material. More particularly, it relates to a fabric reinforced silicone. A method of making fabric reinforced elastomer materials is also disclosed.

BACKGROUND OF THE INVENTION

Elastomer materials have numerous uses in the medical arts. For example, elastomer materials have been used to suspend prosthetic limbs, to provide support joints for limbs in braces, to provide cushioning pads on orthosis devices and to provide compression garments for use in compression therapy. However, finding suitable elastomer materials for these uses has proven problematic.

For example, the elastomer materials used to make suspension sleeves and brace supports must exhibit high compression capabilities which are necessary to keep these devices in place. In addition, suspension sleeves usually have a low coefficient of friction. A low coefficient of friction can be problematic if the compressive force of the sleeve is not adequate which results in the sleeve becoming loose and pistoning to occur. To prevent such pistoning, suspension sleeves are made to fit tightly by using compressive means which oftentimes cause discomfort to the user. The compression capabilities of elastomer materials is also important in compression garments used to treat burn, lymphedema and vascular patients. Pure elastomer materials, having varying compression capabilities are easily cut or nicked and quickly deteriorate. Further, almost all hydrocarbon-based elastomer materials react with skin causing contact dermatitis.

Thus, what is needed then is a reinforced elastomer material that has a high coefficient of friction, that has readily adjustable compression capabilities, that is resistant to tearing and deterioration, that does not cause contact dermatitis, and that is anisotropic, i.e., has greater elongation radially than axially.

In view of the prior art at the time the present invention was made, it was not obvious to those of ordinary skill in the pertinent art how the needed reinforced elastomer materials could be provided.

SUMMARY OF THE INVENTION

The long-standing but heretofore unfulfilled need for reinforced elastomer materials for use in the medical arts is now met by a fabric reinforced elastomer material comprising a first base material, the first base material being an elastic fabric and forming an external surface of the fabric reinforced material; and a second base material, the second base material being an elastomer, the second base material forming a coating of a predetermined thickness on one side of the first base material and interfacing between the first base material and an area of a body being contacted with the fabric reinforced material. The first base material is any elastic woven fabric known in the art, while the second base material is a liquid silicone rubber.

The invention accordingly comprises the features that will be exemplified in the description hereafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 6 is a perspective view of a leg orthosis using the fabric reinforced elastomer material of the present invention;

FIG. 7 is a cross-sectional view of FIG. 6, taken along lines 7—7 thereof; and

DETAILED DESCRIPTION OF THE INVENTION

Figure 1:
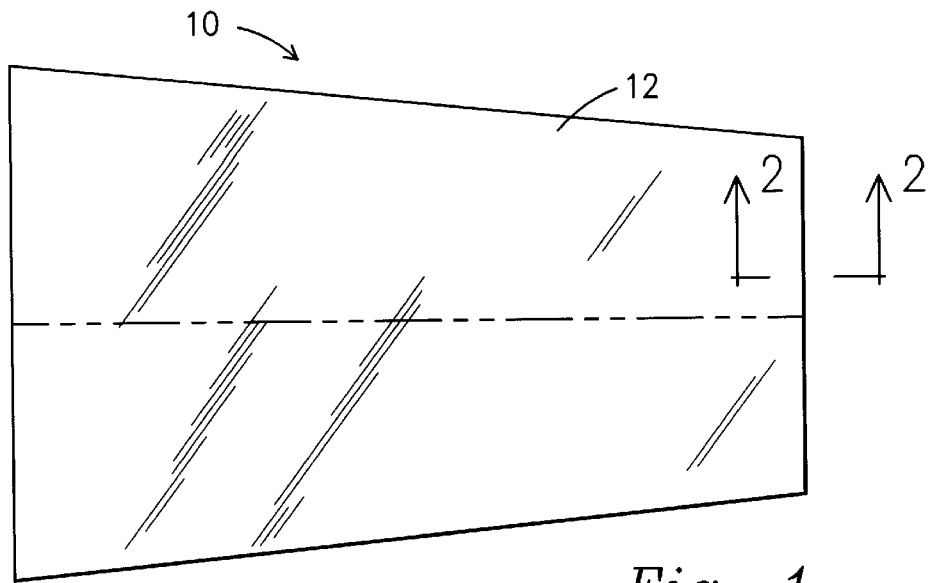
FIG. 1 is a top plan view of the fabric reinforced elastomer material of the present invention.

Referring now to the drawings, in which like numerals refer to like elements thereof, FIG. 1, shows an embodiment of the invention which is denoted as a whole by the reference numeral 10.

Figure 2:
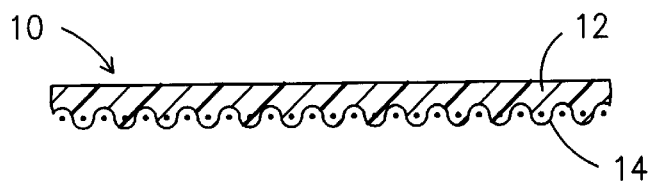
FIG. 2 is a side cross-sectional view of the fabric reinforced elastomer material of FIG. 1, taken along lines 2—2 thereof.

FIG. 2 is a side, cross-sectional view of the fabric reinforced elastomer material of the present invention shown in FIG. 1, taken along lines 1—1 thereof. As shown in FIG. 2 the fabric reinforced elastomer material 10 is a composite structure in which a first base material 12 forms an external surface of the fabric reinforced elastomer material 10 and a second base material 14 forms a coating of a predetermined thickness on one side of the first base material 12. The second base material 14 forms an interface between the first base material 12 and an area of a body being contacted with the fabric reinforced elastomer material 10. For purposes of the present invention, the thickness of the first base material 12 is from 0.005 to 0.04 inches, while in a preferred embodiment the thickness of the first base material 12 is 0.015 inches. The first base material 12 is any elastic fabric known in the art, preferably the first base material 12 is an elastic woven fabric. Further, the elastic woven fabrics useful in the present invention are anisotropic, i.e., they have greater elongation radially than axially. Numerous elastic woven fabrics are known in the art and are suitable for use in the present invention.

The second base material 14 is any elastomer known in the art. The thickness of the second base material 14 is from 0.005 to 0.040 inches, while in preferred embodiments the thickness ranges from 0.010 to 0.020 inches. The second base material 14 is bonded to the first base material 12 by any means known in the art. Preferably the elastomers useful in the present invention are silicones. Any known commercial grade silicone is useful in the present invention. Silicones useful in the present have a durometer (Shore A) hardness of from 5 to 70. Although the use of elongation oils and fillers is contemplated in the present invention, they are not necessary.

The elastic fabric allows the silicone to resist cuts and nicks, which delays the deterioration of the silicone. The fabric reinforced elastomer material of the present invention is particularly useful because portions can be cut out, which increases the comfort of the user, without affecting the durability of the silicone. The low compression and high coefficient of friction of the silicone which forms an interface between the area of the body being treated keeps the sleeve in place without causing discomfort to the user. In addition, the high coefficient of friction of the silicone greatly reduces or eliminates pistoning when the fabric reinforced elastomer material of the present invention is fashioned as a prosthetic sleeve. The silicone does not cause skin reactions. The fabric prevents clothes from clinging to the fabric reinforced elastomer material of the present invention.

Many sizes of fabric reinforced elastomer material 10 sheets are contemplated by the present invention. The fabric reinforced elastomer material 10 sheets are fashioned into sleeves or braces by methods known in the art. The sleeves or braces are produced to fit most patients. In particular, the sleeves or braces have a circumference from six to ten centimeters for children's extremities and up to eighty centimeters for larger sized extremities. Further, it is contemplated that sleeves of the present invention can be fashioned to fit the torso and any other body part requiring treatment.

It is understood by those skilled in the art that the fabric reinforced elastomer material of the present invention is useful as an interface to a prosthetic device, as a brace support or as an orthosis cushion. More particularly, the fabric reinforced elastomer material of the present invention can be fashioned as a suspension sleeve, a brace support, or worn as a cushioning pad for orthosis for various parts of the body.

When the fabric reinforced elastomer material of the present invention is worn on a residual limb it serves as a connective and protective interface between the residual limb and a prosthesis. Further, the fabric reinforced elastomer material of the present invention serves as a protective interface between an area of the body and an orthosis.

In addition, the fabric reinforced elastomer material of the present invention is useful in compression therapy for the treatment of burn, lymphedema and vascular patients. Garments useful in compression therapy can be fashioned by methods known in the art. Compression therapy garments include those for legs, arms, hands, feet, fingers and toes. Further, it is contemplated that garments can also be fashioned for the torso, neck, face and practically every part of the body. These garments can be made with or without an opening and are easily donned by the user. The compressive capabilities of a compression garment can be adjusted to fit the needs and therapeutic regime of the individual user to provide a compression garment which provides appropriate compression. For example, it is known by those skilled in the art that adjustments can be made to the compression capabilities of a compression garment by using elastic fabrics having different elasticities, by using silicones having different durometer (Shore A) hardness characteristics, by using a thicker layer of silicone, by adjusting the size of the compression garment in relation to the actual size of the area being treated or by any combination of the above.

Compression garments made with the fabric reinforced elastomer material of the present invention have several advantages over conventional compression garments, including, but not limited to, increased durability, the inventive garments are easier to clean resulting in better hygiene, the inventive garments are more comfortable to wear due to the non-stick nature of silicone and the inventive garments are not as hot to wear as conventional compression garments. In addition, the inventive garments are particularly useful in treating burn and surgical patients by preventing the formation of hypertrophic scar.

Figure 3:
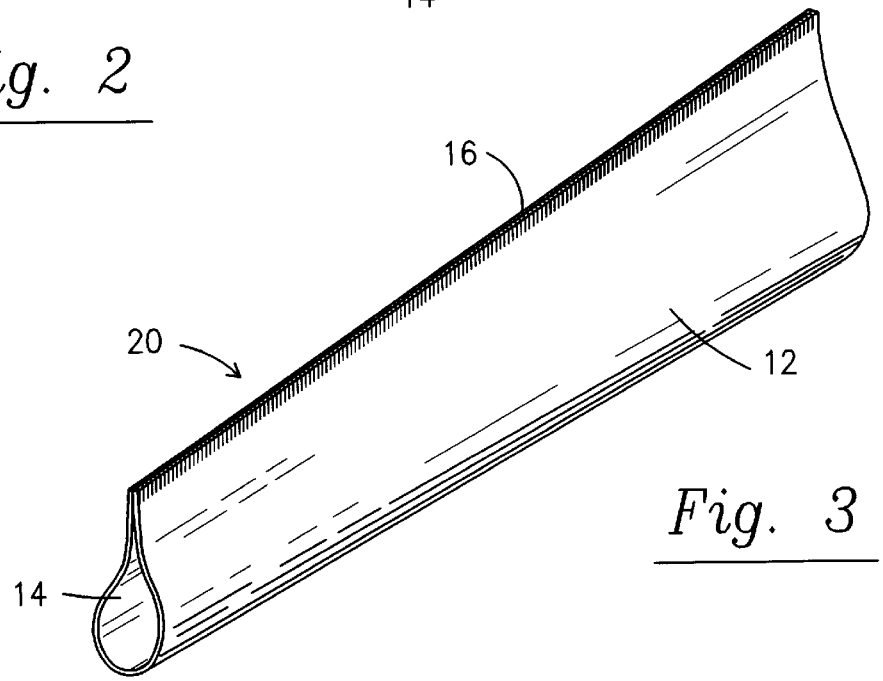
FIG. 3 is a perspective view of a suspension sleeve embodiment of the fabric reinforced elastomer material of the present invention.

As shown in FIG. 3 a suspension sleeve made of the fabric reinforced elastomer material 10 of the present invention can be formed by any means known in the art. For example, the sleeve 20 can by made by sewing together the ends of a sheet of the fabric reinforced elastomer material 10. After sewing the seam 16 is coated with silicone. The first base material 12 forms an external surface of the sleeve 20, while the second base material 14 comes in contact with an area of the body being treated with sleeve 20.

Figure 4:
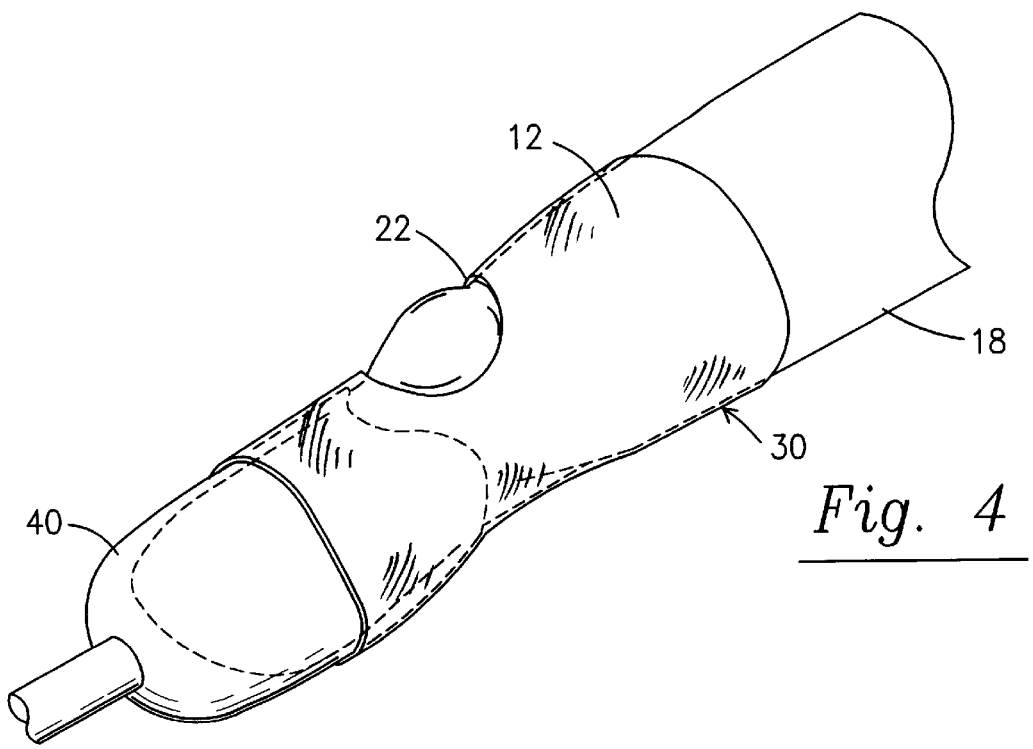
FIG. 4 is a perspective view of a suspension sleeve embodiment of the fabric reinforced elastomer material of the present invention with a prosthesis.

As shown in FIG. 4 the fabric reinforced elastomer material 10 is fashioned into a suspension sleeve 30. The suspension sleeve 30 has an open end to receive a residual limb 18 with the second base material 14 in contact with the skin of residual limb 18. Sleeve 30 also contains a cut-out 22 to allow range of motion of a joint, in this case the knee. The suspension sleeve 30 has a second open end to receive a prosthesis 40. The second base material 14 is in contact with the outer surface of the prosthesis 40. Due to the high coefficient of friction of the silicone, which is the second base material 14, no additional attachment means are necessary on the portion of the sleeve 30 receiving limb 18. However, while additional attachment means are not necessary, any attachment means known in the art may also be used in conjunction with the suspension sleeve 30 of the present invention. Similarly, additional attachment means known in the art, between prosthesis 40 and the sleeve 30 are not necessary, but may be used.

Figure 5:
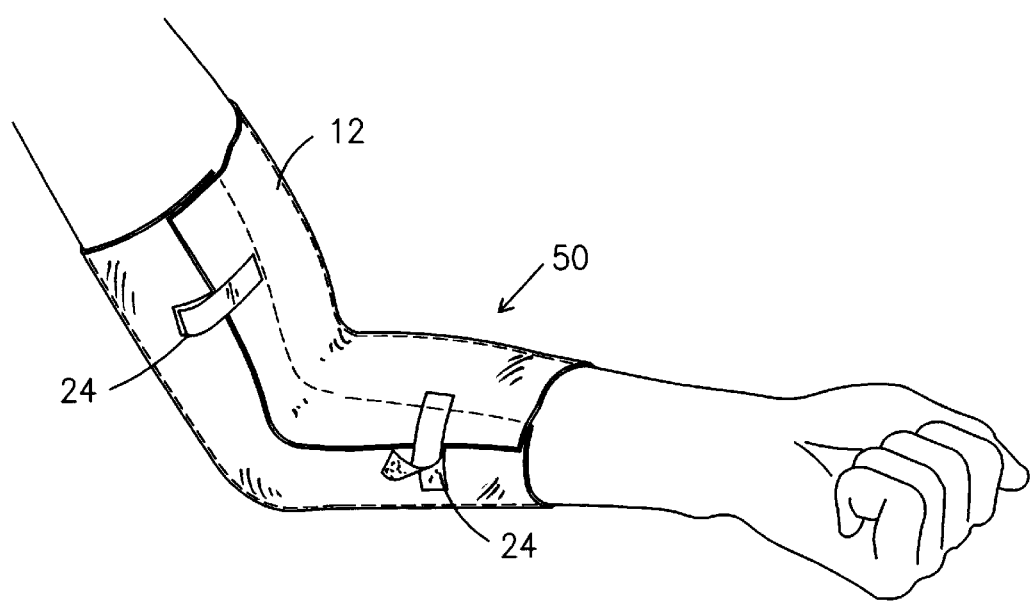
FIG. 5 is a perspective view of another embodiment of the fabric reinforced elastomer material of the present invention on an arm.

Another embodiment 50 of the fabric reinforced elastomer material 10 is shown in FIG. 5. It is contemplated that the embodiment 50 shown in FIG. 5 can be used as either a brace or a compression garment. Embodiment 50 has a closure means 24 which is a hook-and-loop fastener, i.e., VELCRO®. Embodiment 50, when used as a compression garment can be fashioned by methods known in the art to have various compression capabilities, depending on the needs of the user.

In FIGS. 6 and 7, the fabric reinforced elastomer material 10 is shown as a cushion for an orthosis device 42. The fabric reinforced elastomer material 10 is placed on the device 42 where the metal brace 44 may exert pressure and chafe the skin of limb 48, thereby protecting and cushioning the affected area of 48. Specifically, the fabric reinforced elastomer material 10 is configured to cover areas of the orthosis device 42 which may exert pressure on limb 48. Glue 46 is applied to the first base material 12 side, and the device 10 is adhesively attached to the orthosis device 42. Other attachment means are contemplated and any attachment means known to the art may be used. An added benefit of the present invention is that the first base material which is a fabric substantially prevents clothes from clinging to the fabric reinforced elastomer material 10 or parts of the orthosis 42 covered by the fabric reinforced elastomer material 10.

Figure 8:
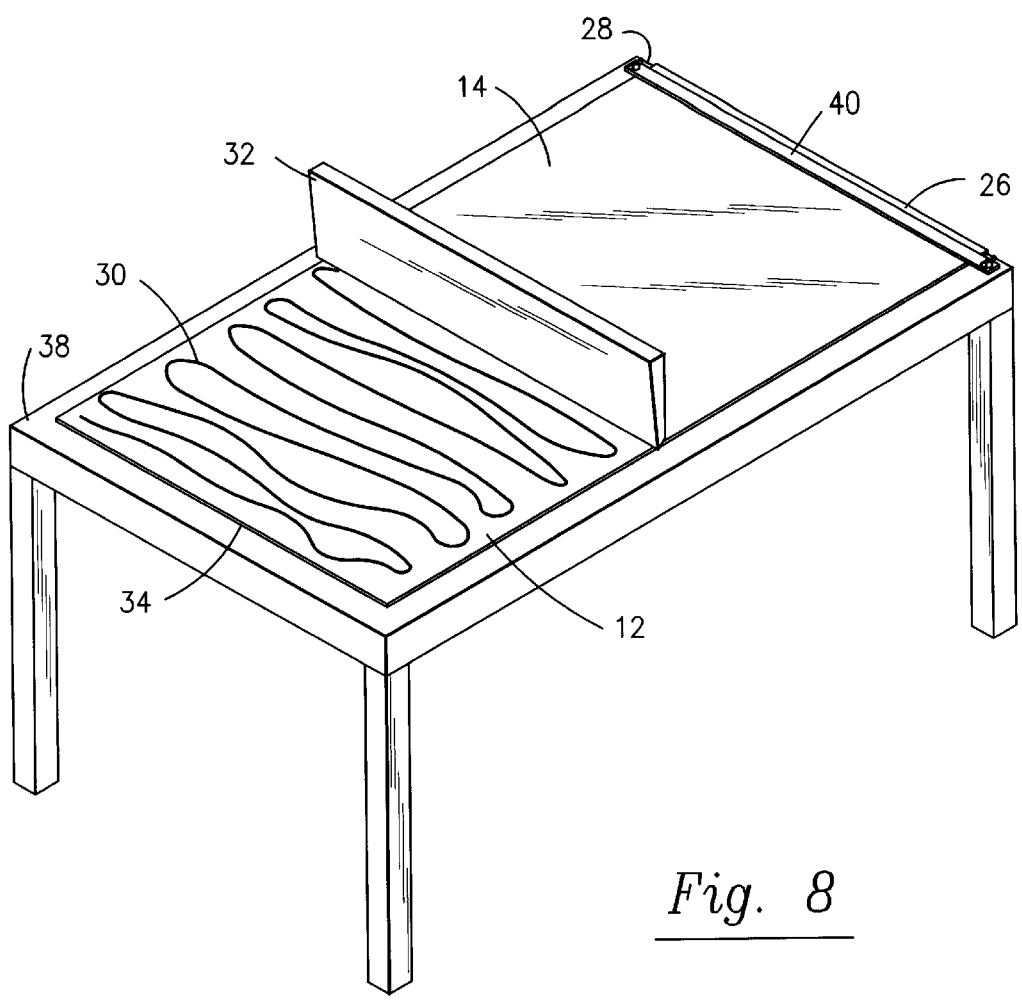
FIG. 8 is an animation that depicts the method of making the fabric reinforced elastomer material of the present invention.

A method of making the fabric reinforced elastomer material 10 is shown as an animation in FIG. 8. As shown in FIG. 8 first base material 12 of a preselected size is placed on a horizontal surface 38. An end 26, of the first base material 12, is fastened by any attachment means known in the art to an end 28 of the horizontal surface 38 so that the first base material 12 is immobile on horizontal surface 38.

Next, a predetermined amount of liquid silicone rubber 30 is placed on the first base material 12. Any known spreading means 32 is placed at a preselected height over the first base material 12 at end 26 and moved towards end 34 of the first base material 12. The spreading means 32 spreads the deposited liquid silicone rubber 30 over the entire surface of the first base material 12 to form a second base material 14. As the spreading means 32 is moved, the first base material 12 is stretched which allows the liquid silicone rubber 30 to enter into the weave of the first base material 12. After spreading the liquid silicone rubber 30 over the first base material 12 to form a layer of the second base material, the liquid silicone rubber 30 is cured by any of the means known in the art. After curing, the fabric reinforced elastomer material 10 is ready for use. Significantly, no adhesives are used to make the fabric reinforced material 10. While not wishing to be bound by any one theory it is believed that a natural adhesion between the first base material 12 and the second base material 14 is created during the manufacturing process.

It will thus be seen that the objects set forth above, and those made apparent from the foregoing description, are efficiently attained and since certain changes may be made in the foregoing construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:

1. A fabric reinforced elastomer material, comprising:
    a first base material, the first base material being an elastic woven fabric and forming a substantially flat external surface of a fabric reinforced material; and
    a second base material, the second base material being an elastomer forming a coating of a predetermined thickness on one side of the first base material, said second base material further being integrally cured within the first base material elastic woven fabric wherein the cross-section of the first base material and the second base material is substantially uniform throughout thereby forming a smooth elastomer uniformly compressive interface between the first base material and an area of a body being contacted with the fabric reinforced material.

2. The fabric reinforced elastomer material of claim 1 wherein the second base material is a silicone rubber.

3. A fabric reinforced elastomer device worn on an area of a body, comprising:
    a first base material, the first base material being an elastic woven fabric and forming a substantially flat external surface of a fabric reinforced elastomer device; and
    a second base material, the second base material being an elastomer forming a coating of a predetermined thickness on one side of the first base material, said second base material further being integrally cured within the first base material elastic woven fabric wherein the cross-section of the first base material and the second base material is substantially uniform throughout thereby forming a smooth elastomer uniformly compressive interface between the first base material and an area of a body being contacted with the device.

4. The fabric reinforced elastomer device of claim 3 wherein the second base material is a silicone rubber.

5. A fabric reinforced elastomer device worn on a residual limb and forming a connective interface between a residual limb and a prosthesis, comprising:
    a first base material, the first base material being an elastic woven fabric and forming a substantially flat external surface of a fabric reinforced device and interfacing with a prosthesis; and
    a second base material, the second base material being an elastomer forming a coating of a predetermined thickness on one side of the first base material, said second base material further being integrally cured within the first base material elastic woven fabric wherein the cross-section of the first base material and the second base material is substantially uniform throughout thereby forming a smooth elastomer uniformly compressive interface between the first base material and a residual limb.

6. The fabric reinforced elastomer device of claim 5 wherein the second base material is a silicone rubber.

7. A fabric reinforced elastomer device worn on a limb and forming a protective interface between a limb and an object, comprising:
    a first base material, the first base material being an elastic woven fabric and forming an external surface of a fabric reinforced device and interfacing with an object; and
    a second base material, the second base material being an elastomer forming a coating of a predetermined thickness on one side of the first base material, said second base material further being integrally cured within the first base material elastic woven fabric wherein the cross-section of the first base material and the second base material is substantially uniform throughout thereby forming a smooth elastomer uniformly compressive interface between the first base material and a limb.

8. The fabric reinforced elastomer device of claim 7 wherein the second base material is a silicone rubber.

* * * * *